(12) United States Patent
Chen et al.

(10) Patent No.: US 10,942,181 B2
(45) Date of Patent: Mar. 9, 2021

(54) METHOD AND KIT FOR QUANTIFYING VACCINE

(71) Applicant: Adimmune Corporation, Taichung (TW)

(72) Inventors: Juine-Ruey Chen, Yilan County (TW); Chia-Ying Wu, Taichung (TW); Yung-Tsung Chen, Taichung (TW)

(73) Assignee: Adimmune Corporation, Taichung (TW)

( * ) Notice: Subject to any disclaimer, the term of this patent is extended or adjusted under 35 U.S.C. 154(b) by 28 days.

(21) Appl. No.: 16/421,501

(22) Filed: May 24, 2019

(65) Prior Publication Data

US 2019/0293650 A1 Sep. 26, 2019

Related U.S. Application Data

(60) Provisional application No. 62/648,352, filed on Mar. 26, 2018.

(51) Int. Cl.
| | | |
|---|---|---|
| *G01N 33/569* | (2006.01) | |
| *A61K 39/145* | (2006.01) | |
| *A61K 39/02* | (2006.01) | |
| *A61K 39/39* | (2006.01) | |
| *C07K 14/005* | (2006.01) | |
| *A61K 39/00* | (2006.01) | |

(52) U.S. Cl.
CPC ..... *G01N 33/56983* (2013.01); *A61K 39/025* (2013.01); *A61K 39/145* (2013.01); *A61K 39/39* (2013.01); *C07K 14/005* (2013.01); *A61K 2039/55505* (2013.01)

(58) Field of Classification Search
CPC ...... A61K 2300/00; A61K 2039/55516; A61K 48/0091; A61K 39/12; A61K 39/145; A61K 48/00; A61K 2039/525; A61K 39/245; A61K 2039/5258; A61K 2039/5158; C12N 2760/14134; C12N 2760/18534; C12N 2710/16122; C12N 2710/16222; C12N 2760/16134; G01N 33/56983; G01N 33/54306; G01N 33/53; G01N 33/5308; G01N 2415/00; G01N 2500/04; C07K 14/05; C07K 16/3092; A61L 2202/22; A61L 2/0017; A61L 2/022; G16H 20/10; A61B 5/1112; B01L 2300/0864; C07H 11/04; C08L 101/00; C11C 3/06

See application file for complete search history.

(56) References Cited

U.S. PATENT DOCUMENTS

| | | | | |
|---|---|---|---|---|
| 2004/0047882 | A1* | 3/2004 | Broeker | A61K 39/39 424/206.1 |
| 2012/0269852 | A1* | 10/2012 | Kersten | A61P 31/16 424/210.1 |

OTHER PUBLICATIONS

Hansen et al. Vaccine 2009, vol. 27, issue 6, pp. 888-892.*
Thermo Scientific in Inatructions Micro BCA Protein Assay Kit published by 2015.*
Rinella Jr. Journal of Colloid and International Science, 1998, vol. 205, pp. 161-165.*
Huang et al. International Journal of Pharmaceutics, 2014, vol. 466, pp. 139-146.*
Jully et al. Pharmaceutical Biotechnology 2015, vol. 104, pp. 557-565.*
Costa et al. Journal of Virological Methods, 2011, vol. 172, pp. 32-37.*

* cited by examiner

*Primary Examiner* — Bao Q Li
(74) *Attorney, Agent, or Firm* — ScienBiziB, P.C.

(57) ABSTRACT

The present disclosure provides a method for quantifying a vaccine. The method includes the steps of: 1) providing a plurality of standard mixtures, each of the standard mixtures having a standard antigen and an aluminum based adjuvant; 2) mixing a stabilizing solution with the vaccine and each of the standard mixtures; 3) determining dosages of the standard antigens in the standard mixtures to establish a standard curve; and 4) determining a dosage of a target antigen in the vaccine according to the standard curve.

11 Claims, 12 Drawing Sheets

METHOD AND KIT FOR QUANTIFYING VACCINE

CROSS-REFERENCE TO RELATED APPLICATION

The present disclosure claims the benefit of U.S. provisional application No. 62/648,352, filed on Mar. 26, 2018, the entirety of which is incorporated herein by reference.

FIELD OF THE DISCLOSURE

The present disclosure relates to a quantification method, particularly to a method of quantifying vaccines.

BACKGROUND OF THE DISCLOSURE

Adjuvants may be added to a vaccine to boost the immune response of a human body, so as to improve production of antibodies and last immunity. Therefore, less antigen is needed for adjuvant containing vaccines to achieve a desired immunological response. There are various adjuvants for boosting immune responses, and their mechanisms to boost immunity may vary.

Vaccine manufacturers needs to ensure the quality of mass produced vaccine products. One of the steps in quality control of the vaccines is to quantify the antigens in the vaccine. Quantifying the antigen ensures the consistency of the concentration and dosage of the antigens in the vaccine.

A conventional method for quantifying antigens in a vaccine is the bicinchoninic acid (BCA) assay. The BCA assay determines the total concentration of protein in a solution. However, the adjuvant in the vaccine interferes the specificity and binding ability of antibodies when BCA assay is used to quantify the antigens in the vaccine. Therefore, the adjuvant has to be separated from the vaccine prior to quantifying the antigens in the vaccine. However, separating the adjuvant from the vaccine can be time-consuming and costly; sensitivity and accuracy of the quantification may also be affected.

BRIEF SUMMARY OF THE DISCLOSURE

An objective of the present disclosure is to provide a method for simplifying and improving the sensitivity and accuracy of vaccine quantification.

An embodiment of the present disclosure provides a method for quantifying a vaccine. The method includes the steps of: 1) providing a plurality of standard mixtures, each of the standard mixtures comprising a standard antigen and an aluminum based adjuvant; 2) mixing a stabilizing solution with the vaccine and each of the standard mixtures; 3) determining dosages of the standard antigens in the standard mixtures to establish a standard curve; and 4) determining a dosage of a target antigen in the vaccine according to the standard curve.

Preferably, the dosages of the standard antigens are determined by measuring a standard absorbance of each of the standard antigens, and the standard curve is established according to the standard absorbances.

Preferably, the dosage of the target antigen is determined by measuring an absorbance of the target antigen and referencing the absorbance to the standard curve.

Preferably, the dosages of the standard antigens and the dosage of the target antigen are determined by using an immunoassay.

Preferably, the target antigen of the vaccine comprises a viral protein fragment.

Preferably, the standard antigen comprises at least a part of the viral protein fragment.

Preferably, the vaccine is an enterovirus 71 (EV71) vaccine, a Japanese encephalitis vaccine, or an influenza vaccine.

Preferably, the aluminum based adjuvant is aluminum hydroxide ($Al(OH)_3$), aluminum phosphate ($AlPO_4$) or aluminum sulfate ($Al_2(SO_4)_3$).

Preferably, a volume ratio of the stabilizing solution to the vaccine is 1:9.

Preferably, a volume ratio of the stabilizing solution to one of the standard mixtures is 1:9.

Preferably, the stabilizing solution is hydrochloric acid (HCl), trichloroacetic acid ($CCl_3COOH$), acetic acid ($CH_3COOH$) or nitric acid ($HNO_3$).

Preferably, a pH of the stabilized solution falls within a range of 9 to 12.

Preferably, the stabilizing solution is sodium hydroxide (NaOH), potassium hydroxide (KOH), calcium hydroxide ($Ca(OH)_2$), sodium bicarbonate ($NaHCO_3$) or ammonium hydroxide ($NH_4OH$).

An another embodiment of the present disclosure provides a kit for quantifying a vaccine. The kit includes a plurality of standard mixtures; each of the standard mixtures includes a standard antigen; an aluminum based adjuvant; and a stabilizing solution. A dosage of a target antigen in the vaccine is determined according to a standard curve established from dosages of the standard antigens.

Preferably, the aluminum based adjuvant is aluminum hydroxide ($Al(OH)_3$), aluminum phosphate ($AlPO_4$) or aluminum sulfate ($Al_2(SO_4)_3$).

Preferably, the stabilizing solution is hydrochloric acid (HCl), trichloroacetic acid ($CCl_3COOH$), acetic acid ($CH_3COOH$) or nitric acid ($HNO_3$).

Preferably, a pH of the stabilizing solution falls within a range of 9 to 12.

Preferably, the stabilizing solution is sodium hydroxide (NaOH), potassium hydroxide (KOH), calcium hydroxide ($Ca(OH)_2$), sodium bicarbonate ($NaHCO_3$), or ammonium hydroxide ($NH_4OH$).

In sum, according to various embodiments of the present disclosure, by mixing the stabilizing solution with the vaccine, the vaccine quantification method is simplified and sensitivity and accuracy thereof are also improved.

BRIEF DESCRIPTION OF THE DRAWINGS

The accompanying drawings illustrate one or more embodiments of the present embodiment and, together with the written description, explain the principles of the present disclosure. Wherever possible, the same reference numbers are used throughout the drawings to refer to the same or like elements of an embodiment.

In accordance with common practice, the various described features are not drawn to scale and are drawn to emphasize features relevant to the present disclosure. Like reference characters denote like elements throughout the figures and text.

DETAILED DESCRIPTION OF THE PREFERRED EMBODIMENTS

Figure 1:
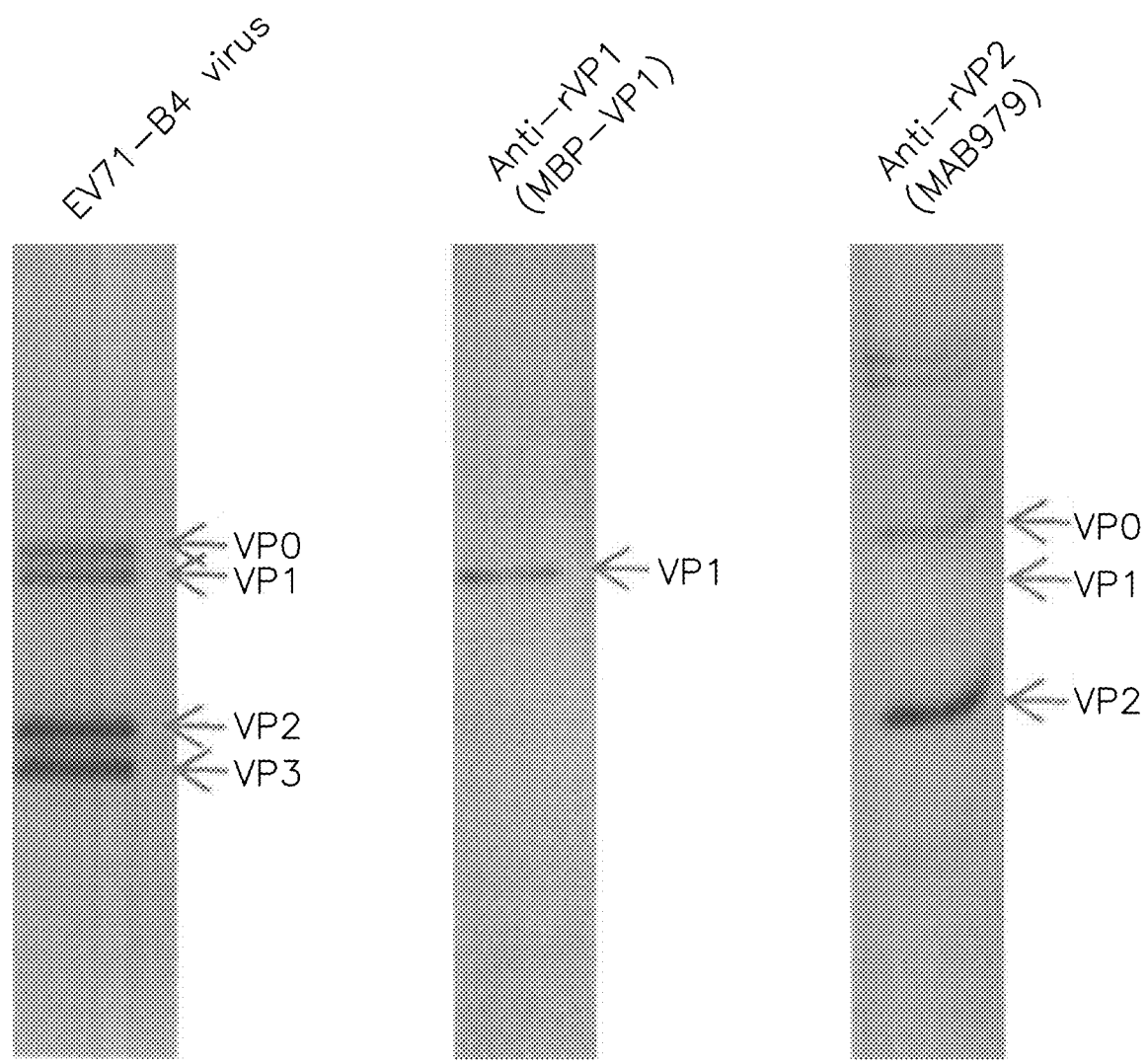
FIG. 1 is an SDS/Western blot image showing the specificity of anti-rVP1 and anti-rVP2 to EV71 antigens.

The present disclosure will now be described more fully hereinafter with reference to the accompanying drawings illustrating various exemplary embodiments of the present disclosure. The present disclosure may, however, be embodied in many different forms and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

It will be understood that the terms "and/or" and "at least one" include any and all combinations of one or more of the associated listed items. It will also be understood that, although the terms first, second, third etc. may be used herein to describe various elements, components, regions, parts and/or sections, these elements, components, regions, parts and/or sections should not be limited by these terms. These terms are only used to distinguish one element, component, region, part or section from another element, component, region, layer or section. Thus, a first element, component, region, part or section discussed below could be termed a second element, component, region, layer or section without departing from the teachings of the present disclosure.

The present disclosure will be further elaborated below with reference to specific examples, and within each of the examples, several standard mixtures with different compositions and/or pH values are provided. The following examples and materials described hereafter are for exemplary purposes only.

In an embodiment of the present disclosure, a method for quantifying a vaccine includes the steps of: 1) providing a plurality of standard mixtures, each of the standard mixtures having a standard antigen and an aluminum based adjuvant; 2) mixing a stabilizing solution with the vaccine and each of the standard mixtures; 3) determining dosages of the standard antigens in the standard mixtures to establish a standard curve; and 4) determining a dosage of a target antigen in the vaccine according to the standard curve.

Specifically, in Step 1, a standard mixture is provided. A plurality of Enterovirus containing standard mixtures (EVS) with a series of known concentrations of Enterovirus (EV) antigens (e.g., 4.0 μg/ml, 2.5 μg/ml, 2.0 μg/ml, 1.5 μg/ml, 1.0 μg/ml, and 0.5 μg/ml) are prepared. The concentrations of the EV antigens in the EVS are determined by bicinchoninic acid (BCA) assay. Thereafter, the EVS are each mixed with an aluminum based adjuvant (e.g., 600 μg/ml of $Al(OH)_3$) to produce a standard mixture containing 300 μg/ml of $Al(OH)_3$. In some embodiments, the aluminum based adjuvant may be, but is not limited to, aluminum phosphate ($AlPO_4$) or aluminum sulfate ($Al_2(SO_4)_3$). The EV in the EVS may be Japanese Encephalitis or Influenza virus. In the embodiment, a volume ration of the EVS to $Al(OH)_3$ is 1:1 in the standard mixture. The standard mixtures may be stored at 2-8° C. overnight.

In Step 2: the vaccine and the standard mixtures are each mixed with a stabilizing solution. After the standard mixtures are prepared, the standard mixtures and the vaccine having an unknown concentration of target antigens (EVV) are mixed with a stabilizing solution. The stabilizing solution may be an alkali solution that includes sodium hydroxide (NaOH), potassium hydroxide (KOH), calcium hydroxide ($Ca(OH)_2$), sodium bicarbonate ($NaHCO_3$), ammonium hydroxide ($NH_4OH$), or any combination thereof. In a preferred embodiment, the stabilizing solution may be 0.025-0.1M of NaOH. Alternatively, the stabilizing solution may be an acid solution that includes hydrochloric acid (HCl), trichloroacetic acid ($CCl_3COOH$), acetic acid ($CH_3COOH$), nitric acid ($HNO_3$), or any combination thereof. In another preferred embodiment, the stabilizing solution may be 10% V/V of acetic acid. The EVV (or the vaccine to be quantified) may be a Japanese Encephalitis vaccine or an Influenza vaccine. A volume ratio of the stabilizing solution to one of the standard mixtures may be 1:9, and a volume ratio of the stabilizing solution to one of the EVVs may be 1:9. After mixed with the stabilizing solution, the EVV and the standard mixtures are incubated at 37° C. for 18-20 hours.

It is to be noted that the aluminum based adjuvant may become more soluble under basic or acidic conditions. In an embodiment, a chemical reaction between $Al(OH)_3$ and the acid solution is $Al_3^+{}_{(aq)} + 3H_2O_{(l)} \leftrightarrows 3H^+{}_{(aq)} + Al(OH)_{3(aq)}$; likewise, a chemical reaction between $Al(OH)_3$ and the alkali solution is $Al(OH)_{3(s)} + OH^-{}_{(aq)} \leftrightarrows Al(OH)_4^-{}_{(aq)}$.

In Step 3: A standard curve is established. In an embodiment, the stabilizing solution containing standard mixtures are coated on a 96-well Enzyme-Linked ImmunoSorbent Assay) plate at 2-8° C. overnight. The absorbances of the EV antigens in the standard mixtures are measured by enzyme-linked immunosorbent Assay (ELISA) using a specific antibody. A standard curve is established according to the ELISA measured absorbances of the EV antigens in each of the standard mixtures.

Since the EV antigens have two epitopes VP1 and VP2, MBP-VP1 (anti-rVP1) or MAB979 (anti-rVP2) antibodies may be used for detection of the EV antigens. In an SDS/Western blot analysis as shown in FIG. 1, both of the anti-rVP1 and anti-rVP2 antibodies were shown to exhibit good specificity to EV71 antigens.

In Step 4: A dosage of the target antigens in the EVV is determined according to the standard curve. The EVV is coated on a 96-well plate at 2-8° C. overnight. The absorbance of the target antigens (e.g., EV71 antigens) in the EVV is measured by ELISA using specific antibodies, such as the MBP-VP1 (anti-rVP1) or MAB979 (Anti-rVP2) antibodies. Thereafter, the absorbance of the target antigen is referenced to the standard curve established in Step 3 to obtain a concentration of the target antigens in the vaccine. In the embodiments of the present disclosure, the concentration of the target antigens is referred to as the dosage of the target antigens.

Figure 2:
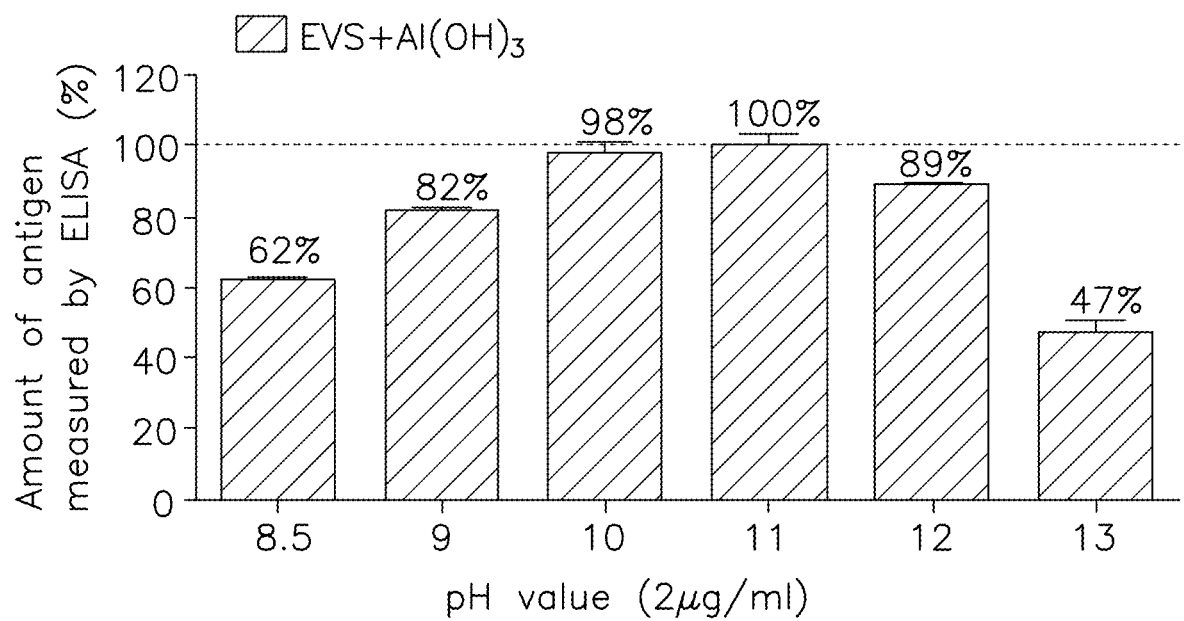
FIG. 2 is an experimental result showing the effect of the pH of a NaOH solution on the amount of detectable EV71 antigens.

Example 1: Effect of pH of the Stabilizing Solution on Quantifying Antigens in the EVS As shown in FIG. 2, at least 80% of the EV71 antigens in the EVS are retained after the EVS is mixed with an NaOH solution having a pH higher than 9.0 and lower than 12.0. Therefore, a preferred pH of the alkali solution for quantifying the target antigens (e.g., EV71 antigens) in the vaccine may fall within a range of 9-12.

Figure 3:
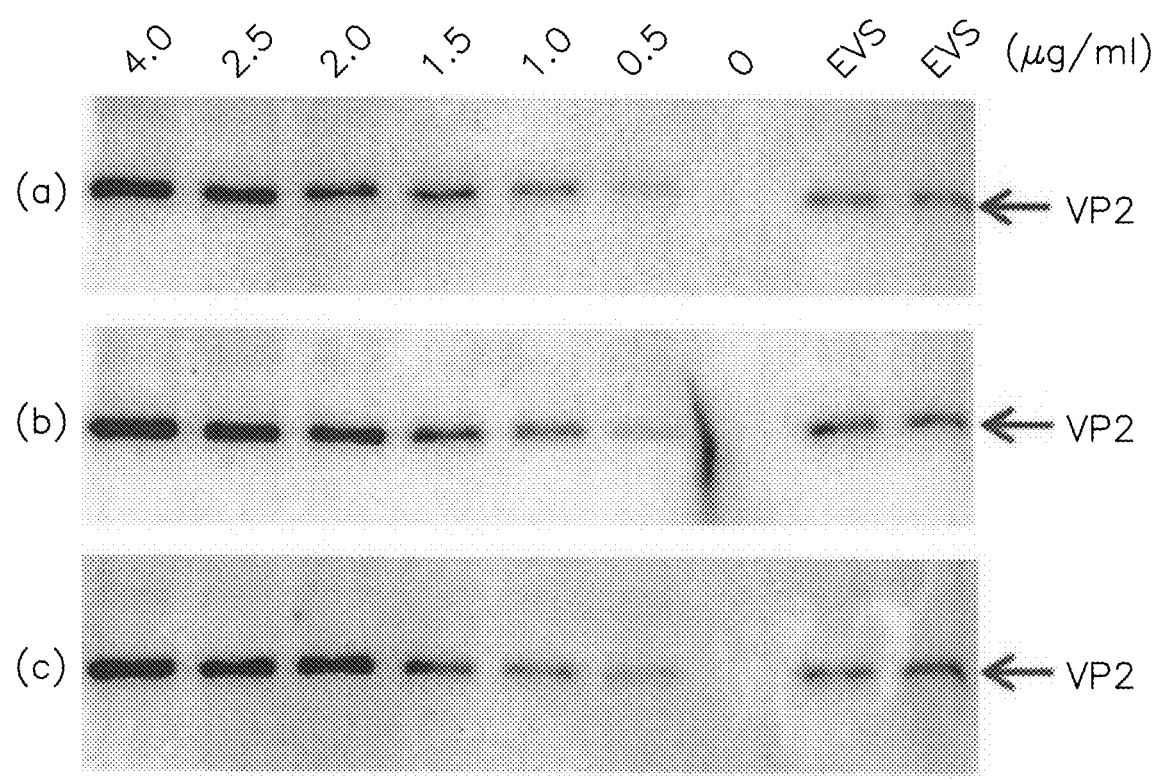
FIG. 3 is a Western blot image showing the integrity of EV71 antigens in the standard mixture after being mixed with the NaOH solution.

Example 2: Effect of Alkali Solution on Integrity of the Antigens to be Quantified in the Vaccine To investigate the integrity of EV71 antigens after being mixed with the alkali solution, the NaOH containing EVS is analyzed by Western blot using anti-rVP2 antibodies. As shown in FIG. 3, three repetitions examined using a series of antigen concentrations (e.g., 4.0 µg/ml, 2.5 µg/ml, 2.0 µg/ml, 1.5 µg/ml, 1.0 µg/ml, 0.5 µg/ml, and 0 µg/ml) consistently demonstrate that the alkali solution does not affect the integrity of EV71.

Figure 4:
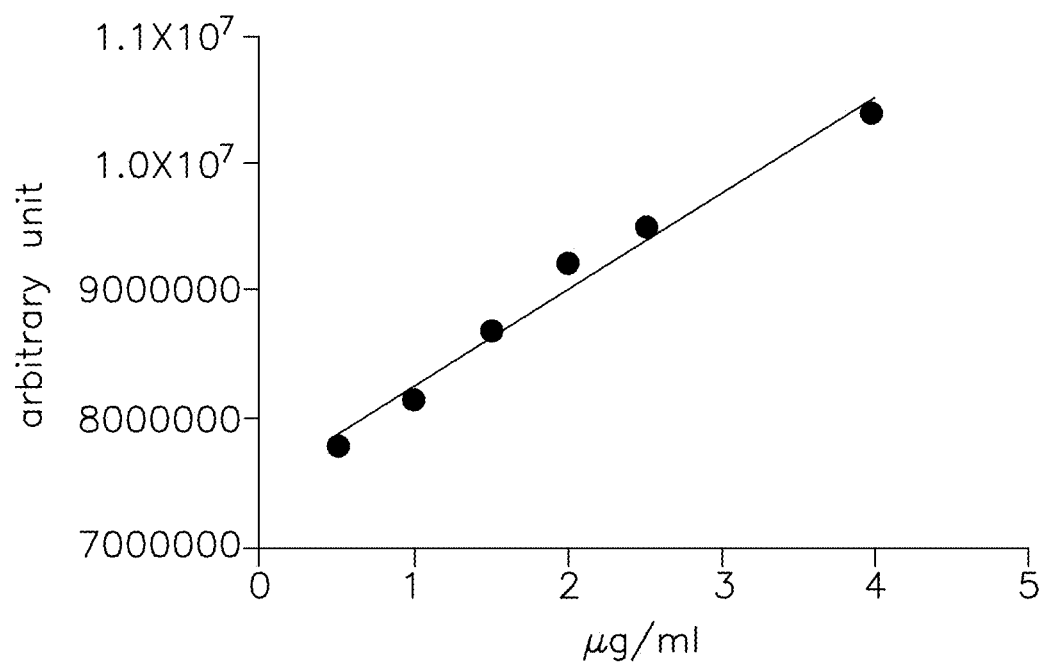
FIG. 4 is a standard curve obtained according to an embodiment of the present disclosure.

The antigens in the NaOH containing standard mixtures may also be quantified by enhanced chemiluminescence (ECL) Western blot. As shown in FIG. 4, the standard curve of average concentrations of the antigens in each of the standard mixtures as determined by ECL Western blot exhibit a fitting of y=754616x+7.515e+006, $r^2$=0.97. The average concentrations are each calculated according to three repetitions.

Figure 5:
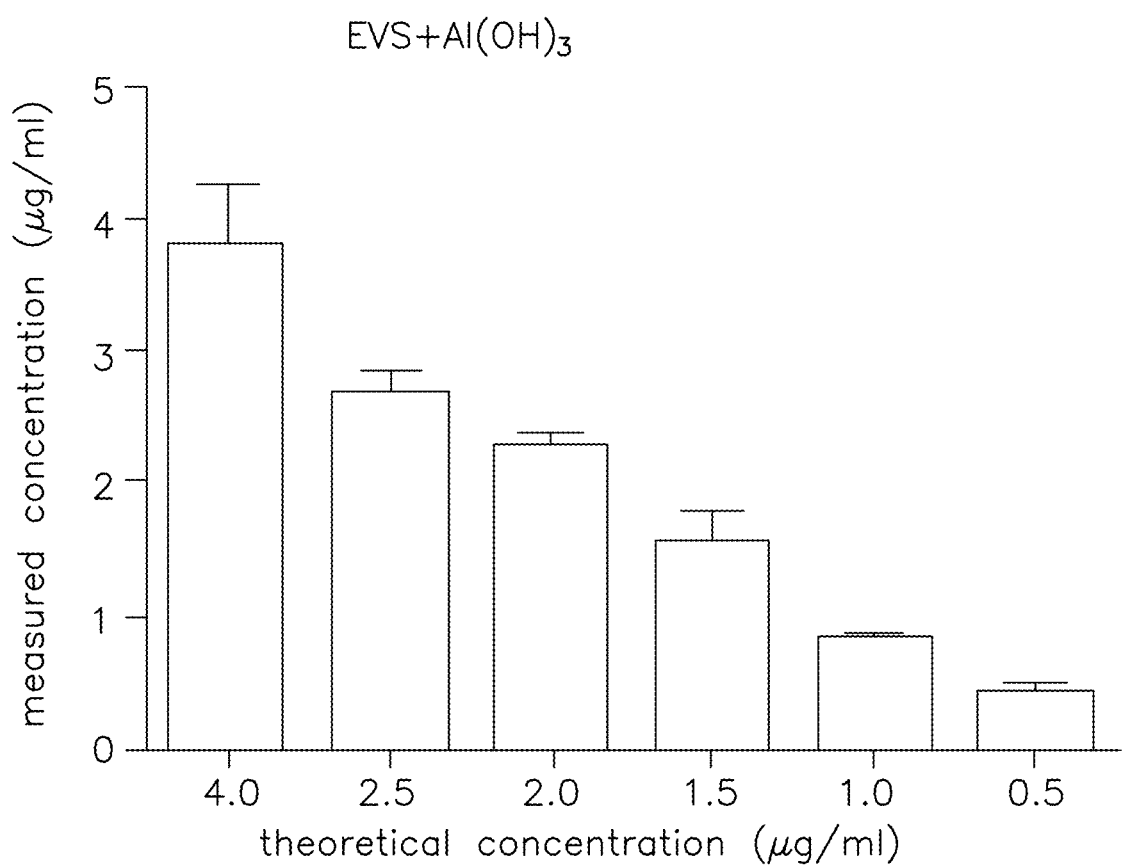
FIG. 5 is a bar chart showing the accuracy and precision of the quantification method according to an embodiment of the present disclosure.

FIG. 5 is a bar chart showing the average concentrations and coefficient of variations (CVs) of the antigens in each of the standard mixtures as measured by ECL Western blot. As shown in FIG. 5, the measured concentrations are generally close to the theoretical concentrations, and the CV among three repetitions for each concentration is lower than 20%. The results demonstrate that the alkali solution is suitable for quantifying the antigens with high accuracy and precision.

Figure 6:
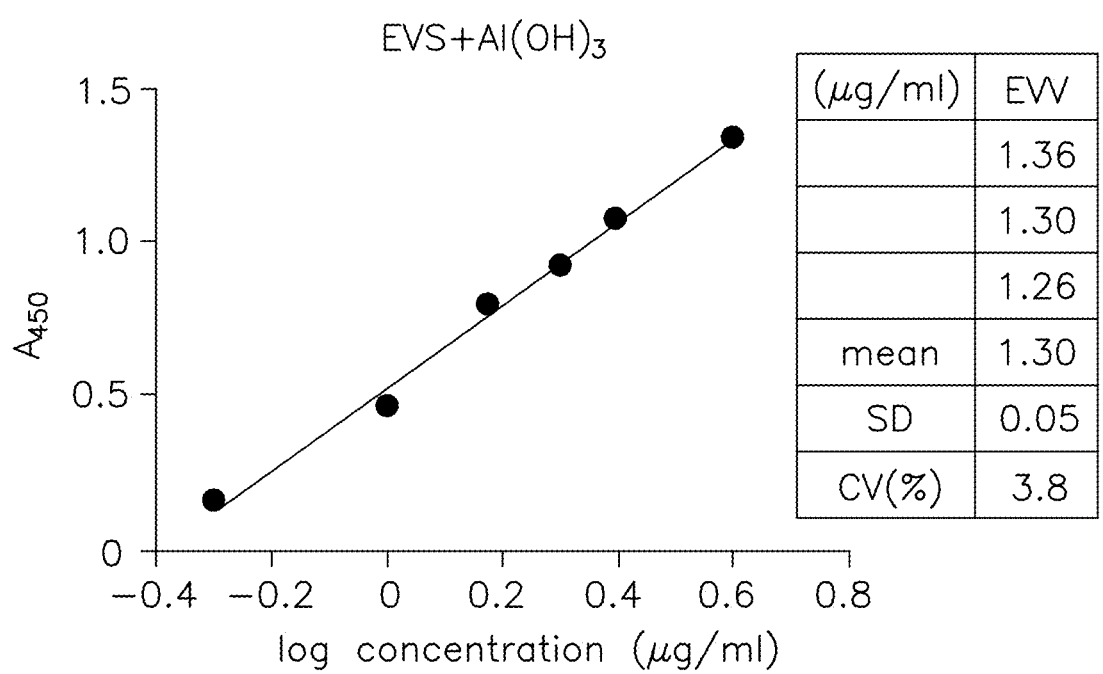
FIG. 6 is a standard curve obtained according to an embodiment of the present disclosure.

To further verify the effect of the alkali solution on quantifying the antigens in the vaccine, each of the standard mixtures mixed with NaOH is measured by ELISA using anti-rVP2 antibodies. Each of the concentrations is examined for three times, and an average concentration is calculated accordingly. As shown in FIG. 6, the standard curve of the average concentrations of the antigens in the standard mixtures as determined by the ELISA exhibit a fitting of y=1.348x+0.5351, $r^2$=0.99. Furthermore, the target antigens in EVV are also measured by the same approach for three times (resulting in 1.36 µg/ml, 1.30 µg/ml, and 1.26 µg/ml, respectively). As shown in the Table in FIG. 6, the log average concentration of the target antigens in the EVV is determined to be 1.30±0.05 µg/ml, with a CV of 3.8%. The result is also indicative of the high accuracy and precision of the quantification method.

Figure 7:
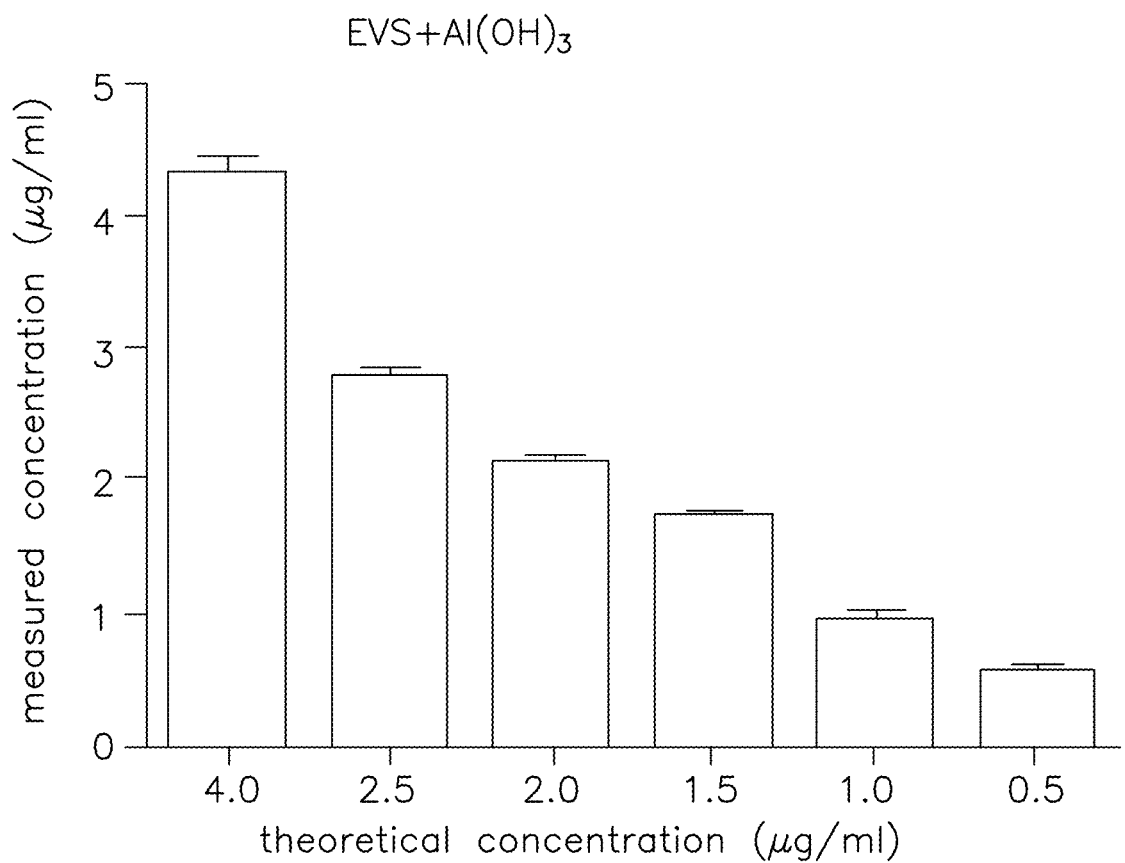
FIG. 7 is a bar chart showing the accuracy and precision of the quantification method according to an embodiment of the present disclosure.

FIG. 7 is a bar chart showing the average concentrations of the antigens in each of the standard mixtures as measured by ELISA using anti-rVP2 antibodies. As shown in FIG. 7, the measured concentrations are generally close to the theoretical concentrations, and the CV among three repetitions is lower than 4.24%. The results again suggest the accuracy and precision of the quantification method.

Furthermore, Table 1 shows the measured concentrations of antigens in the standard mixtures and the accuracy of the measured concentrations according to FIGS. 6 and 7.

TABLE 1

Using anti-rVP2 to quantify the antigens

| Standard mixture | Standard mixture (EVS + Al(OH)$_3$) | | | | |
|---|---|---|---|---|---|
| Theoretical concentration (µg/ml) | Measured concentration (µg/ml) and accuracy % | | | Average | Standard deviation |
| 4 | 4.08 | 3.88 | 4.07 | 4.01 | 0.11 |
|   | 98 | 97 | 98 | 97.7 | 0.6 |
| 2.5 | 2.52 | 2.59 | 2.60 | 2.57 | 0.04 |
|   | 99 | 96 | 96 | 97.3 | 1.8 |
| 2 | 1.98 | 1.97 | 1.94 | 1.96 | 0.02 |
|   | 99 | 98 | 97 | 98.1 | 0.9 |
| 1.5 | 1.57 | 1.59 | 1.59 | 1.58 | 0.01 |
|   | 96 | 94 | 94 | 94.6 | 0.8 |
| 1 | 0.92 | 0.91 | 0.85 | 0.89 | 0.03 |
|   | 92 | 91 | 85 | 89.2 | 3.4 |
| 0.5 | 0.54 | 0.52 | 0.52 | 0.53 | 0.01 |
|   | 92 | 95 | 96 | 94.7 | 1.9 |

As shown in Table 1, the standard deviation between the average theoretical concentrations and measured concentrations of the antigens are below 15%. The results demonstrate the accuracy of the quantification method of the present embodiment.

Figure 8:
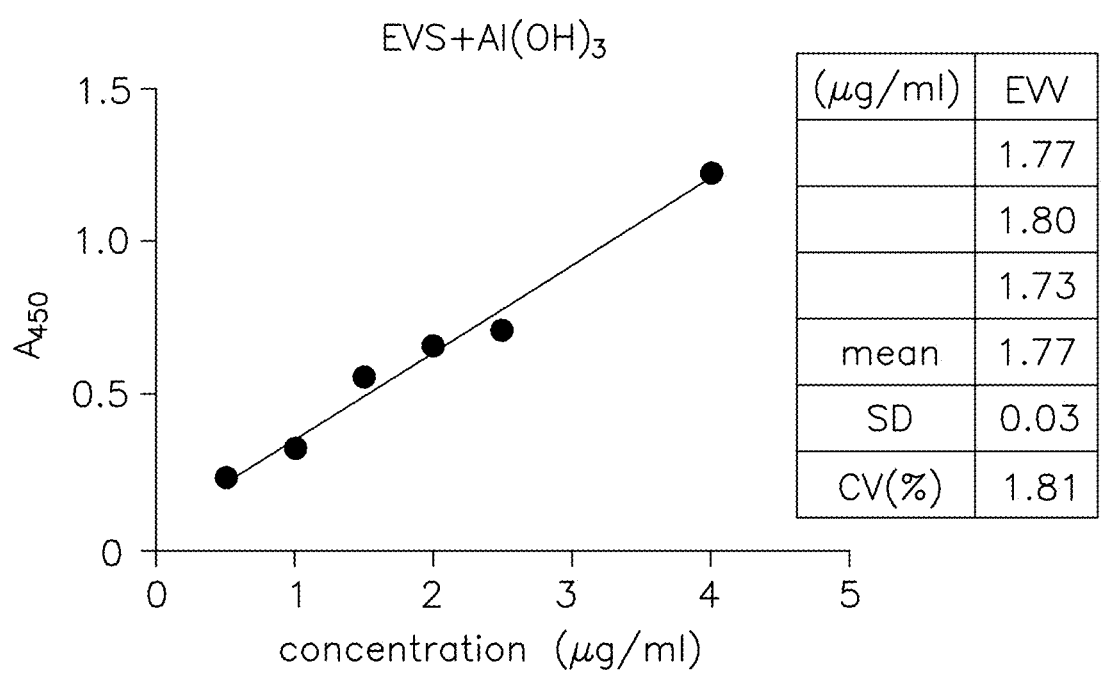
FIG. 8 is a standard curve obtained according to an embodiment of the present disclosure.

In addition to using anti-rVP2 antibodies as described in FIG. 6 and FIG. 7, anti-rVP1 antibodies are also utilized to verify the accuracy and precision of the quantification method provided by the embodiments of the present disclosure. Similar to the aforementioned, each of the standard mixtures mixed with NaOH is measured by ELISA using anti-rVP1 antibodies. Each of the concentration is repeatedly tested for three times, and an average concentration of the antigens is calculated accordingly. As shown in FIG. 8, the standard curve of average concentrations of the antigens in each of the standard mixtures as determined by ELISA using anti-rVP1 antibodies exhibit a fitting of y=0.2835x+0.08561, $r^2$=0.98. Furthermore, the target antigens in the EVV are also measured for three times (resulting in 1.77 µg/ml, 1.80 µg/ml, and 1.73 µg/ml, respectively). As shown in the Table in FIG. 8, the average concentration of the target antigens in the EVV is determined to be 1.77±0.03 µg/ml, with a CV of 1.81%. The results again demonstrate the high accuracy and precision of the quantification method.

Figure 9:
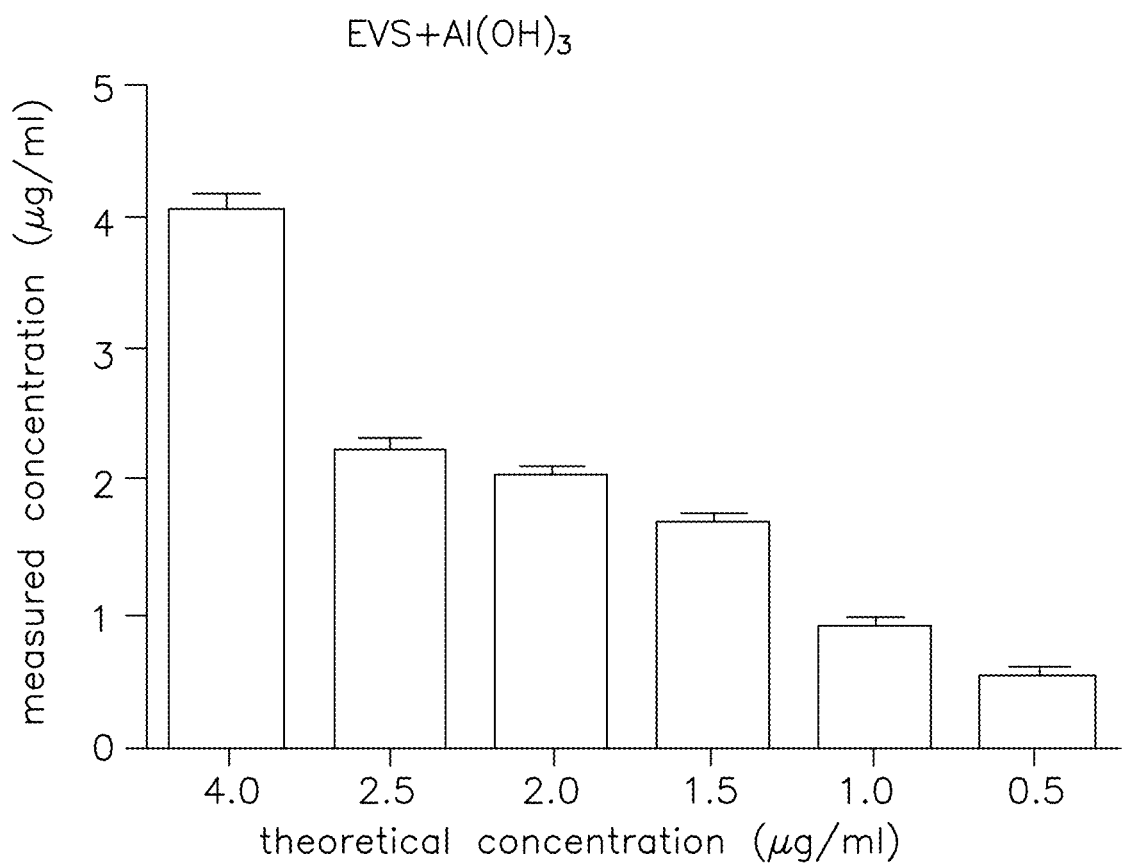
FIG. 9 is a bar chart showing the accuracy and precision of the quantification method according to an embodiment of the present disclosure.

FIG. 9 is a bar chart showing that the average concentrations of the antigens in each of the standard mixtures as measured by ELISA using anti-rVP1 antibodies. As shown in FIG. 9, the measured concentrations are generally close to the theoretical concentrations, and the CV among three repetitions is lower than 5.44%. The results not only suggest the accuracy and precision of the quantification method, but indicate that quantifying by ELISA is more precise than quantifying by Western blot.

Furthermore, Table 2 shows the measured concentrations of antigens in the standard mixtures and the accuracy of the measured concentrations according to FIGS. 8 and 9.

TABLE 2

Using anti-rVP1 to quantify the antigens

| Standard mixture | standard mixture (EVS + Al(OH)$_3$) | | | | |
|---|---|---|---|---|---|
| Theoretical concentration (μg/ml) | Measured concentration (μg/ml) and accuracy % | | | Average | Standard deviation |
| 4 | 4.15 | 4.13 | 3.97 | 4.08 | 0.10 |
|   | 96 | 97 | 99 | 97.0 | 1.6 |
| 2.5 | 2.28 | 2.29 | 2.16 | 2.24 | 0.07 |
|   | 91 | 92 | 87 | 90.0 | 2.8 |
| 2 | 2.10 | 2.04 | 2.02 | 2.05 | 0.04 |
|   | 95 | 98 | 99 | 97.0 | 2.1 |
| 1.5 | 1.69 | 1.75 | 1.65 | 1.70 | 0.05 |
|   | 87 | 83 | 90 | 87.0 | 3.1 |
| 1 | 0.90 | 0.94 | 0.84 | 0.89 | 0.05 |
|   | 90 | 94 | 84 | 89.0 | 4.9 |
| 0.5 | 0.51 | 0.56 | 0.53 | 0.53 | 0.03 |
|   | 99 | 88 | 94 | 94.0 | 5.3 |

As shown in Table 2, the standard deviation between the average theoretical concentrations and measured concentrations of the antigens are below 15%. The results demonstrate the accuracy of the quantification method of the embodiment of the present disclosure.

As shown in Table 3, when the theoretical concentrations of EVVs are 2.0 μg/ml and 1.0 μg/ml the standard deviation between the measured concentrations as determined by using anti-rVP1 or anti-rVP2 antibodies and theoretical concentrations are lower than 15%. Therefore, the quantification method of the present embodiment is highly accurate and precise.

TABLE 3

Using anti-rVP2 or anti-rVP1 to quantify target antigens in EVVs

| Theoretical concentration (μg/ml) | Anti-rVP2 (Mab979) | Anti-rVP1 | Mean ± STD |
|---|---|---|---|
| 2 (μg/ml) | 1.86 ± 0.14 | 2.1 ± 0.1 | 1.98 ± 0.17 |
| accuracy (%) | 93.0 ± 7.2 | 95.0 ± 6.0 | 94.0 ± 1.4 |
| CV (%) | 7.5 | 4.8 | — |
| 1 (μg/ml) | 0.98 ± 0.07 | 0.86 ± 0.1 | 0.94 ± 0.06 |
| accuracy (%) | 94.3 ± 4.5 | 85 ± 4.6 | 90.0 ± 6.6 |
| CV (%) | 7.1 | 11.6 | — |

Example 3: Effect of Acid Solution on Quantification of Antigens

Figure 10:
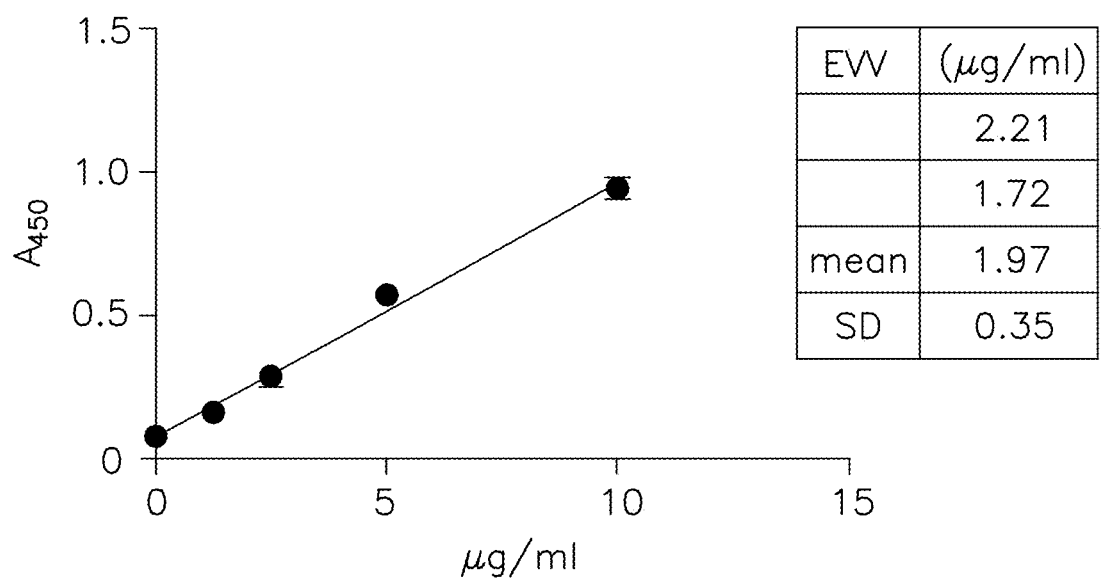
FIG. 10 is a standard curve obtained according to an embodiment of the present disclosure.

To verify the effect, each of the standard mixtures mixed with acetic acid is subjected to ELISA using anti-rVP2 antibodies. Each of the concentrations (e.g., 10 μg/ml, 5 μg/ml, 2.5 μg/ml, 1.25 μg/ml and 0 μg/ml) is measured for three times, and an average concentration of the antigens in each of the standard mixtures is calculated accordingly. As shown in FIG. 10, the standard curve of the average concentrations of the antigens in each of the standard mixtures as determined by the ELISA exhibit a fitting of y=0.08938x+ 0.07025, $r^2$=0.99. Furthermore, the target antigens in EVV are also measured twice (resulting in 2.21 μg/ml and 1.72 μg/ml, respectively). As shown in the Table in FIG. 10, the average concentration of the target antigens in the EVV is determined to be 1.97±0.35 μg/ml.

Figure 11:
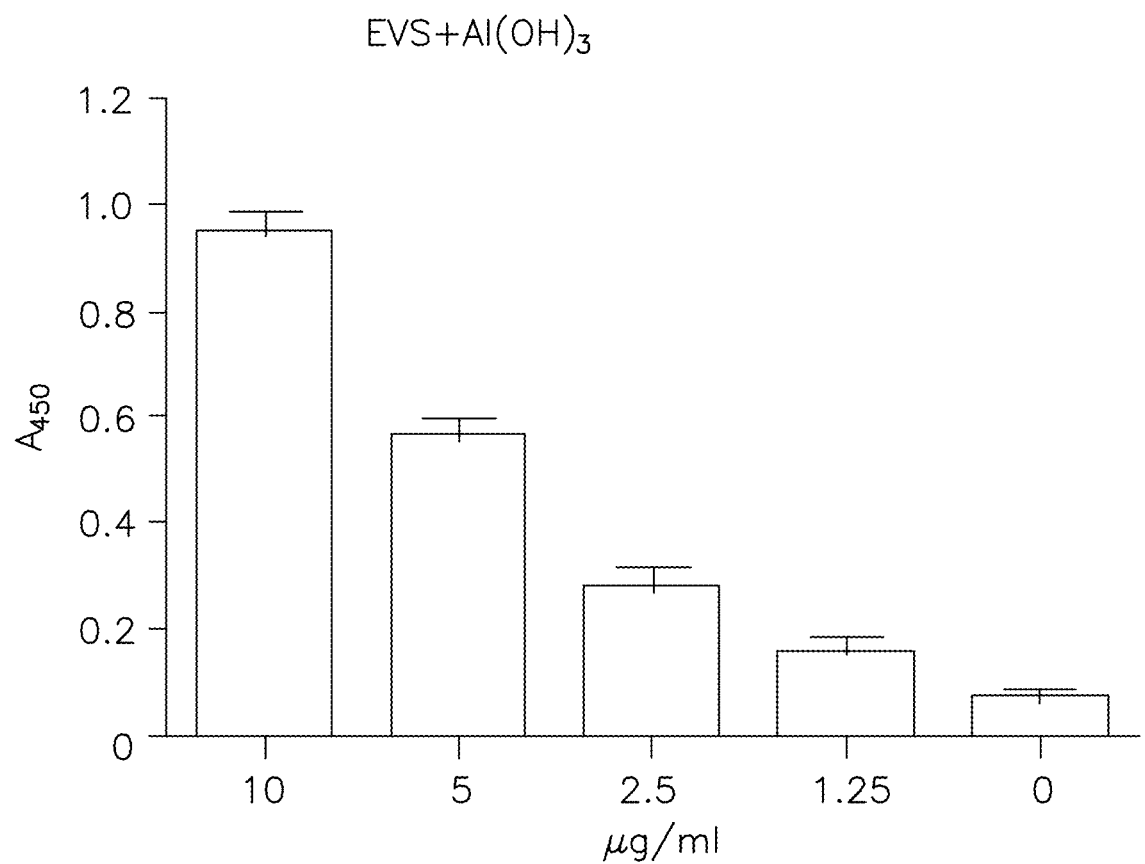
FIG. 11 is a bar chart showing the accuracy and precision of the quantification method according to an embodiment of the present disclosure.

FIG. 11 is a bar chart showing the average concentrations of the antigens in each of the standard mixtures as measured by ELISA using anti-rVP2 antibodies. As shown in FIG. 11, the CV among three repetitions for each of the standard mixtures is lower than 20%.

Figure 12:
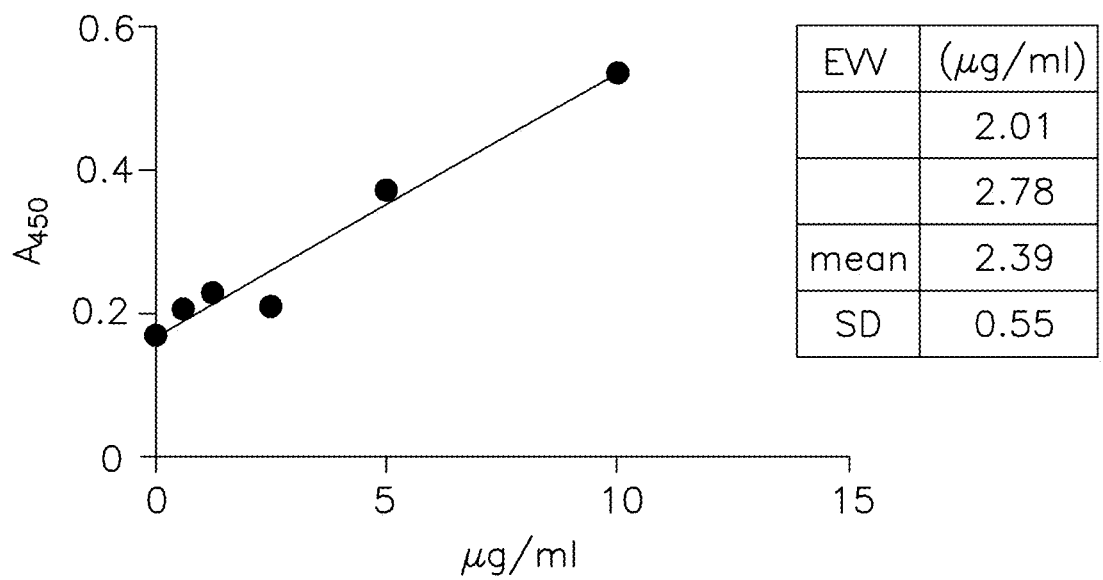
FIG. 12 is a standard curve obtained according to an embodiment of the present disclosure.

In FIG. 12, each of the standard mixtures mixed with acetic acid is measured by ELISA using anti-rVP1 antibodies. Each of the concentrations (e.g., 10 μg/ml, 5 μg/ml, 2.5 μg/ml, 1.25 μg/ml and 0 μg/ml) is examined for three times, and an average concentration of the antigens is calculated accordingly. As shown in FIG. 12, the standard curve of the average concentrations of the antigens in the standard mixtures as determined by the ELISA exhibit a fitting of y=0.03488x+0.1576, $r^2$=0.97. Furthermore, the target antigens in the EVV is also measured twice (resulting in 2.01 μg/ml and 2.78 μg/ml, respectively). As shown in FIG. 12, the average concentration of the target antigens in the EVV is determined to be 2.39±0.55 μg/ml.

In sum, according to various embodiments of the present disclosure, by mixing the stabilizing solution with the vaccine, the vaccine quantification method is simplified and sensitivity and accuracy thereof are ensured.

Previous descriptions are only embodiments of the present disclosure and are not intended to limit the scope of the present disclosure. Many variations and modifications according to the claims and specification of the disclosure are still within the scope of the claimed disclosure. In addition, each of the embodiments and claims does not have to achieve all the advantages or characteristics disclosed. Moreover, the abstract and the title only serve to facilitate searching patent documents and are not intended in any way to limit the scope of the claimed disclosure.

What is claimed is:

1. A method for quantifying a vaccine containing an aluminum based adjuvant, comprising:
    1) providing a plurality of standard mixtures containing a series of known concentration of standard antigens;
    2) mixing the aluminum based adjuvant with the each of the standard mixtures to produce a plurality of standard solutions;
    3) mixing a stabilizing solution having a pH falls within a range of 10 to 12 with the vaccine containing the aluminum based adjuvant;
    4) mixing the stabilizing solutions having a pH falls within a range of 10 to 12 with each of the standard solutions;
    5) determining dosages of the standard antigens in the standard to establish a standard curve; and
    6) determining a dosage of a target antigen in the vaccine according to the standard curve.

2. The method according to claim 1, wherein the dosages of the standard antigens are determined by measuring a standard absorbance of each of the standard antigens, and the standard curve is established according to the standard absorbances.

3. The method according to claim 1, wherein the dosage of the target antigen is determined by measuring an absorbance of the target antigen and referencing the absorbance to the standard curve.

4. The method according to claim 1, wherein the dosages of the standard antigens and the dosage of the target antigen are determined by using an immunoassay.

5. The method according to claim 1, wherein the target antigen of the vaccine comprises a viral protein fragment.

6. The method according to claim 5, wherein the standard antigen comprises at least a part of the viral protein fragment.

7. The method according to claim 1, wherein the vaccine is an enterovirus 71 (EV71) vaccine.

8. The method according to claim 1, aluminum based aluminum adjuvant is hydroxide ($Al(OH)_3$), aluminum phosphate ($AlPO_4$) or aluminum sulfate ($Al_2(SO_4)_3$).

9. The method according to claim 1, wherein a volume ratio of the stabilizing solution to the vaccine is 1:9.

10. The method according to claim 1, wherein a volume ratio of the stabilizing solution to one of the standard mixtures is 1:9.

11. The method according to claim 1, wherein the stabilizing solution is sodium hydroxide (NaOH), potassium hydroxide (KOH), calcium hydroxide ($Ca(OH)_2$), sodium bicarbonate ($NaHCO_3$) or ammonium hydroxide ($NH_4OH$).

* * * * *